(12) United States Patent
Hagopian et al.

(10) Patent No.: US 8,976,362 B2
(45) Date of Patent: Mar. 10, 2015

(54) SYSTEM, APPARATUS AND METHOD FOR EMITTANCE CONTROL AND SUPPRESSING STRAY LIGHT

(75) Inventors: John G. Hagopian, Harwood, MD (US); Stephanie A. Getty, Washington, DC (US); Manuel A. Quijada, Laurel, MD (US)

(73) Assignee: USA as represented by the Administrator of the National Aeronautics Space Administration, Washington, DC (US)

( * ) Notice: Subject to any disclaimer, the term of this patent is extended or adjusted under 35 U.S.C. 154(b) by 0 days.

(21) Appl. No.: 13/570,100

(22) Filed: Aug. 8, 2012

(65) Prior Publication Data
US 2014/0043615 A1    Feb. 13, 2014

(51) Int. Cl.
    *G01N 21/47*    (2006.01)
(52) U.S. Cl.
    USPC .................................................. 356/446
(58) Field of Classification Search
    USPC .................................................. 356/446
    See application file for complete search history.

(56) References Cited

U.S. PATENT DOCUMENTS

| | | | |
|---|---|---|---|
| 2009/0246625 A1* | 10/2009 | Lu ................................. | 429/207 |
| 2010/0279209 A1* | 11/2010 | Jeong et al. .................. | 429/518 |
| 2010/0317939 A1* | 12/2010 | Kuhn et al. .................. | 600/323 |
| 2011/0253971 A1* | 10/2011 | Bandyopadhyay .............. | 257/9 |

* cited by examiner

*Primary Examiner* — Tu Nguyen

(57) ABSTRACT

A system, apparatus and method employing carbon nanotubes on substrates such as silicon, titanium, copper, stainless steel and other substrates, where the carbon nanotubes are blacker than existing paints and coatings, thereby providing an exponential increase in stray light suppression depending on the number of bounces of such treated surfaces. Additionally, the present invention is directed to techniques to better absorb and radiate unwanted energies. Further, the alternate substrates offer strength of material for numerous components and in numerous physical applications. The present invention is also directed to techniques for improving the adhesion of the nanotubes to the alternate substrate materials and also extending the wavelength of operation from the near ultraviolet to the far infrared portion of the spectrum (0.2 microns to 120 microns wavelength).

19 Claims, 9 Drawing Sheets

SYSTEM, APPARATUS AND METHOD FOR EMITTANCE CONTROL AND SUPPRESSING STRAY LIGHT

ORIGIN OF THE INVENTION

The invention described herein was made by an employee of the United States Government, and may be manufactured and used by or for the Government for governmental purposes without the payment of any royalties thereon or therefor.

BACKGROUND OF THE INVENTION

1. Field of the Invention

The present invention is in the technical field of improving the capability of equipment for usage in space, atmospheric, oceanic and terrestrial exploration through usage of compositions and materials that suppress stray light and provide enhanced emittance. The principles of the present invention are applicable to any imaging or image projecting system for commercial or scientific use.

2. Description of Related Art

The exploration of space requires equipment with ever-increasing sensitivities to uncover further mysteries of the Universe and its workings. Whether telescopes or other observational instrumentation, the problems of stray light interfering with the performance of these delicate devices are prevalent. Various paints and coatings have helped to absorb stray photons, thereby minimizing some of the ill-effects of this radiation, but further improvements are needed to conquer this deleterious situation for astronomical observation and other measures. Likewise, various atmospheric and terrestrially-based apparatus suffer the same problems.

For example, scientific instrument performance can be limited by stray light from bright sources adjacent to dim objects under observation. A darker material to suppress this stray light has multiple benefits to these observations, including a) enabling scientific observations not currently possible, b) increasing observational efficiencies in high contrast scenes, and c) simplifying instruments and lowering their cost by utilizing fewer stray light components and achieving equivalent performance. Bright objects, such as clouds or ice, scatter light off of instrument structures and components and make it difficult to see dim objects from Earth. Similarly, bright stars or celestial objects can scatter light and compromise the ability to view adjacent dim objects.

One technique employed by the prior art is to use black paints, such as Aeroglaze Z306, on satellites and other equipment to suppress the stray light. This and other prior techniques, however, result in at best approximately 4% of the light being reflected, as determined by hemispherical reflectance or total integrated scatter (TIS), described in more detail hereinbelow.

Another problem related to the above is the need for such coatings to be firmly part of a structural component of the equipment, such as apertures, tubes, stops and baffles, since coatings may degrade and fall off in extreme environments, such as in space, oceanic or atmospheric research.

The National Aeronautics and Space Administration (NASA) has been at the forefront of technology for such developments. With the diverse needs of current and upcoming NASA space research, there is a growing need for equipment that has better stray light suppression for use in space, oceanic, atmospheric and terrestrial instrumentation.

Carbon nanotubes, known for their strength, are also black, and offer the possibility for use in suppressing stray light. However, existing techniques grow the carbon nanotubes on a silicon substrate, which is a poor material for numerous stray light components, such as tubes, stops and baffles, due to its more delicate compositional structure. In addition to light suppression, there is a need for materials that provide emittance control for radiating away heat and energy.

There is, therefore, a need for systems, equipment, compositions and methods that provide stray light suppression capabilities, that these coatings better bond to the substrate materials, that the substrate material be strong, and that the combination be able to function properly in difficult and extreme situations and environments.

SUMMARY OF THE INVENTION

The present invention is directed to a system, apparatus and method employing carbon nanotubes on substrates such as silicon, titanium, copper, stainless steel and other substrates, where the carbon nanotubes are blacker than existing paints and coatings, thereby providing an exponential increase in stray light suppression depending on the number of bounces of such treated surfaces. Additionally, the present invention is directed to techniques to better absorb and radiate unwanted energies. Further, the alternate substrates offer strength of material for numerous components and in numerous physical applications. The present invention is also directed to techniques for improving the adhesion of the nanotubes to the alternate substrate materials and also extending the wavelength of operation from the near ultraviolet to the far infrared portion of the spectrum (0.2 microns to 120 microns wavelength).

BRIEF DESCRIPTION OF THE DRAWINGS

While the specification concludes with claims particularly pointing out and distinctly claiming the subject matter that is regarded as forming the present invention, it is believed that the invention will be better understood from the following Detailed Description, taken in conjunction with the accompanying DRAWINGS, where like reference numerals designate like structural and ether elements, in which:

DETAILED DESCRIPTION OF THE INVENTION

Figure 1:
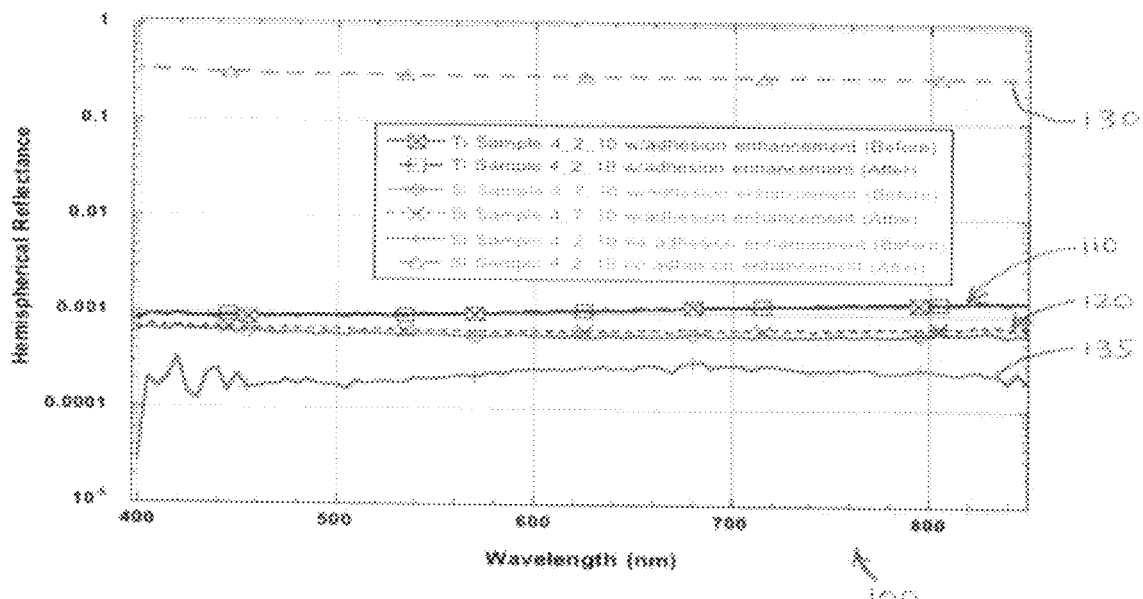
FIG. 1 is a chart illustration of the pre and post results of a tape test performed on various aspects of the instant invention, demonstrating the improvements in adhesion of the nanotubes to prevent degradation (increase) in hemispherical reflectance.

The present invention will now be described more fully hereinafter with reference to the accompanying Drawings, in which preferred embodiments of the invention are shown. It is, of course, understood that this invention may, however, be embodied in many different forms and should not be construed as limited to the embodiments set forth herein; rather, these embodiments are provided so that the disclosure will be thorough and complete, and will fully convey the scope of the invention to those skilled in the art. It is, therefore, to be understood that other embodiments can he utilized and structural changes can be made without departing from the scope of the present invention.

As discussed, various efforts have been employed to minimize the adverse effects of stray light on optical or other equipment used in observation and/or measurement. Existing techniques, such as employing carbon nanotubes solely on silicon, are entirely inadequate for the needs of NASA and other organizations employed in space- or atmospheric-based research, where extremes of environment are the norm. Indeed, the usage of silicon as a substrate has few physical applications due to its rather delicate nature, although many terrestrial uses are, of course, known.

Since their discovery, scientific interest in carbon nanotubes has been motivated by the desire to incorporate and exploit their attractive electrical, mechanical, optical and thermal properties. As a material, carbon nanotubes are lightweight and cost-effective, which fits with NASA's objective for lighter instrumentation. Recently, NASA scientists discovered that carbon nanotubes are ideal stray light absorbers, and provide an order of magnitude improvement over current surface treatments (such as Aeroglaze Z306 black paint), particularly in the UV-visible-near infrared wavelengths of about 200 nanometers to about 2.0 microns, as used in space and earth based telescope instruments. More recently, the advances of the present invention have been increased to wavelengths from about 0.2 microns to about 120 microns and beyond in wavelength, which encompasses the entire infrared to far infrared band of the spectrum.

In these instruments, stray photons contaminate and degrade the images received, causing lower observational efficiencies and unusable data in high contrast regions. An aim of the present invention is to extend this order of magnitude improvement to wavelengths greater than 2.0 microns via increasing the aspect ratio of the nanotubes, which correlates to improved absorption efficiencies at longer wavelengths.

Advances in the fabrication of multiwalled carbon nanotubes (MWCNT) for stray light suppression under recent NASA programs has focused on making this technology practical for use in optical instrumentation. The three most important developments in these ongoing efforts have been: 1) finding a substrate that can survive the high temperature growth process that is a good structural material, 2) improving the broadband absorption properties to make them 10× better than current paints that NASA uses for stray light suppression, and 3) improving adhesion of the nanotubes to the substrate to provide a robust coating that does not easily come off. It should be understood that the factor of 10 advantage afforded by this surface treatment can be exponentially higher in terms of system stray light, as further attenuation occurs during multiple bounces. For example, analyses performed on the present invention indicate factors of 10,000 improvements are possible, although other noise sources can prevent this large gain from being realized.

The titanium and stainless steel embodiments of the present invention were selected as the substrates of choice due to their excellent strength-to-mass ratio and use in many commercial, NASA and military products. The refinement of the adhesion and catalyst layers to optimize the growth process and adhesion of the MWCNTs on titanium and stainless steel, while maintaining broadband absorption, required several modifications to the standard growth process used for MWCNT growth. Many under layers were evaluated to determine their effect on adhesion, and after much trial and error it was determined that alumina provided an excellent adhesion layer for nanotubes grown on titanium, stainless steel and silicon. In application, the alumina adhesion layer should be greater than about 60 nanometers thick to optimize performance, and is at present best applied using electron beam evaporation immediately prior to the deposition of the iron catalyst layer (best thickness of iron is about 1 to 2 nanometers), while maintaining vacuum. It should be understood that other application techniques, such as atomic layer deposition for improved conformal coating to the substrate geometry; are contemplated and within the scope of the present invention.

The decrease in nanotubes lost during a military tape test due to the utilization of this adhesion layer is determined by measuring hemispherical reflectance on a silicon and titanium sample before and after the tape test. For the silicon sample without the alumina adhesion layer, it was found that 100 percent of the nanotubes failed, and the reflectance of the composition increases to that of bare silicon. For the enhanced adhesion titanium and silicon samples of the instant invention, however, there is less than 0.2% change in the absorption after the tape test, as shown in FIG. 1 of the DRAWINGS.

As shown in FIG. 1, an enhanced adhesion MWCNT tape test resulted in a log plot of the hemispherical reflectance of the pre- and post-testing, generally designated by the reference numeral 100. As shown, plotting wavelength in nanometers versus reflectance, the titanium (before and after) treatments are generally designated by the reference numeral 110, showing the pre and post data points nearly coterminous. Likewise for the silicon sample with alumina, generally designated by the reference numeral 120, the pre and post data plots are nearly coterminous, and both demonstrating very low reflectance change. As noted, however, the reflectance of the silicon without the alumina adhesion after the tape test, generally designated by the reference numeral 130, is greatly increased due to the loss of nearly all of the carbon nanotubes, even more than the titanium and silicon with alumina embodiments, with its curve much lower, generally designated by the reference numeral 135.

Copper was selected as an alternate substrate due to its exceptional thermal conductivity, which makes it ideal for calibrator and radiator substrates. Additional substrates, such as chromium and molybdenum may also be employed, although these substrates require additional layers, such as titanium between the substrate and alumina layer.

Accordingly, a procedure for substrate preparation and growth of the MWCNT pursuant to the present invention is as follows.

1. Standard solvent clean in acetone, isopropanol (or ethanol) and water

2. Evaporation: Base pressure ~2e~7 Torr. Electron beam evaporation of 600 to 1200 A of high-purity alumina at rate of 1.0 A/s. Electron beam evaporation of 20-60 A of high-purity iron at a rate of 0.2-0.8 A/s.

3. Growth: atmospheric pressure chemical vapor deposition of multiwalled carbon nanotubes. Purge quartz tube furnace with flowing argon at 800 ccm for 20 minutes. Heat to 750 C at 50 C per minute under flowing argon (800 ccm). Stabilize temperature at 750 C in flowing ultra-high purity hydrogen (2000 ccm) for 5 minutes. Grow CNTs at 750 C in flowing ultra-high purity ethylene (500 ccm) and flowing argon (300 ccm) routed through a water bubbler. Cool down in flowing argon at 300-800 ccm.

Adhesion is further enhanced by including a 10 minute annealing step immediately after the growth at 750 C to 950 C. This allows better anchoring of the nanotubes into the alumina layer.

Following the aforedescribed protocol results in MWCNT's on titanium and alternate substrates that are approximately 50-100 microns in length that appear to be bundled in vertically-oriented clumps 1's to 10's of microns in diameter, as demonstrated in scanning electron microscope imaging of typical growth.

As is understood to one of skill in the art, hemispherical reflectance is a measure of how much light is scattered over pi steradians when light hits a sample. As discussed, this is also called Total Integrated Scatter or TIS. As mentioned, NASA typically uses Aeroglaze Z306 paint as a stray light control.

Figure 2:
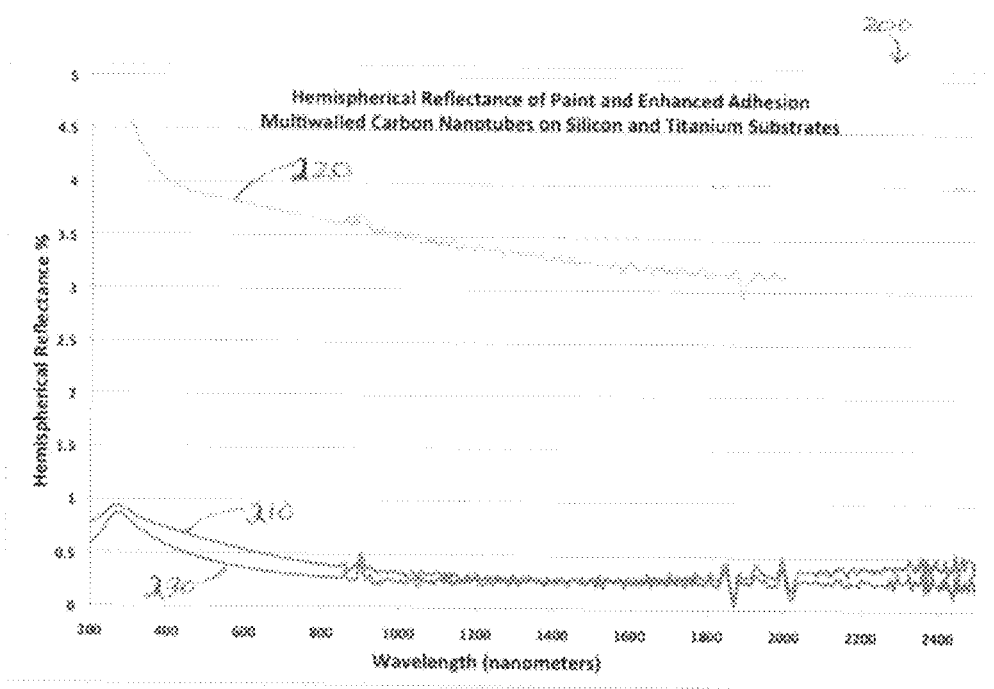
FIG. 2 is a chart illustration of the improved hemispherical reflectance capabilities of the compositions of the present invention over the prior art, demonstrating a greater than 10-fold increase in stray light suppression.

With reference now to FIG. 2 of the DRAWINGS, there is shown a plot, designated by the reference numeral 200, of the hemispherical reflectance of a MWCNT Titanium substrate sample pursuant to the present invention, designated by the reference numeral 210, and of a conventional Z306 paint sample, measured across 200 to 2500 nanometers in wavelength, designated by the reference numeral 220. Also shown is the hemispherical reflectance of a silicon substrate sample, designated by the reference numeral 230. The measurement was performed in a Perkin Elmer Reflectometer. The dramatic decrease in reflectance over a broad spectrum of wavelengths is markedly illustrated in FIG. 2As is understood in the art, in addition to hemispherical reflectance, it is important to understand the reflectance as a function of angle. This is known as the Bidirectional Reflectance Distribution Function or BRDF.

Figure 3:
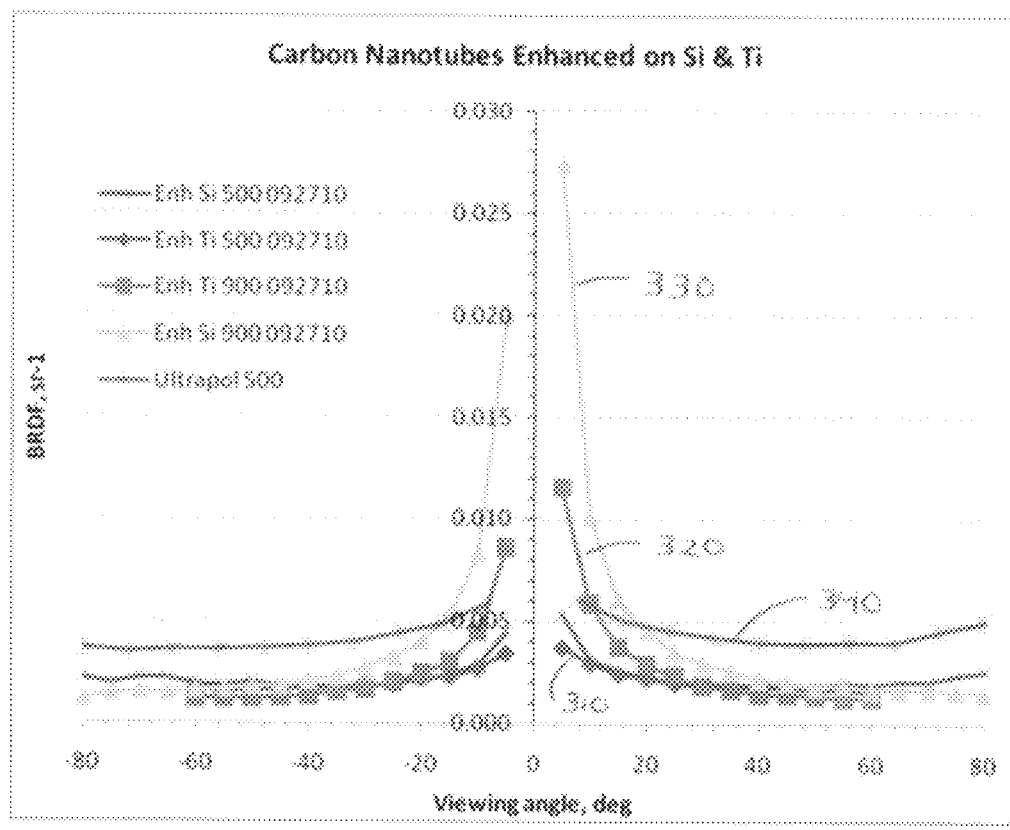
FIG. 3 is another chart illustration of the improved stray light suppression capabilities of the compositions of the present invention over the prior art, illustrating the bidirectional reflectance distribution of the present invention.

With reference to FIG. 3, there is shown the BRDF for enhanced adhesion carbon nanotubes on Silicon and Titanium substrates at 500 and 900 nm wavelengths pursuant to the present invention. In particular, the performance of the enhanced Titanium—carbon nanotube combination of the present invention at 500 nm is designated by the reference numeral 310, and at 900 nm by the reference numeral 320. With further reference to FIG. 3, the BRDF of the Silicon substrate at 900 nm is designated by the reference numeral 330. It is important to note that the Titanium substrate sample is darker than Ultrapol, the performance of which is designated by the reference numeral 340, and which is widely regarded as one of the blackest laboratory references. Ultrapol is, however, unsuitable for many applications due to its fragility. Although not illustrated in FIG. 3, the aforementioned Z306 paint has a BRD that varies between 0.013 and 0.02 over these angles, and which is significantly worse than the Titanium sample.

The current formulation has been refined even further to make it darker. As set forth in the instant application, the approach is to make the carbon nanotubes growth longer, while not adversely affecting the density. Applicant has discovered that high density nanotubes can be longer but more reflective as their effective index of refraction is higher, resulting in a larger reflectance at the interface between the nanotubes and air or vacuum. Therefore, it has been discovered that low density nanotubes with an effective index approaching 1 are ideal, which results in approximately a 1% fill factor of carbon in the nanotube forest. However, a focus of this innovation is the use of titanium as a substrate carrier, which is well suited to make stray light control elements, such as baffles, stops, tubes, laser cavities, etc. This technology is widely applicable to nearly all optical (and some non-optical) instrumentation. It should, of course, be understood that the principles of the present invention may be applicable in a variety of areas beyond optical and the like. An example of a non-optical application is the use as a baffle to prevent emission of ultraviolet photons in mass spectrometers that could degrade measurement accuracy.

Figure 4:
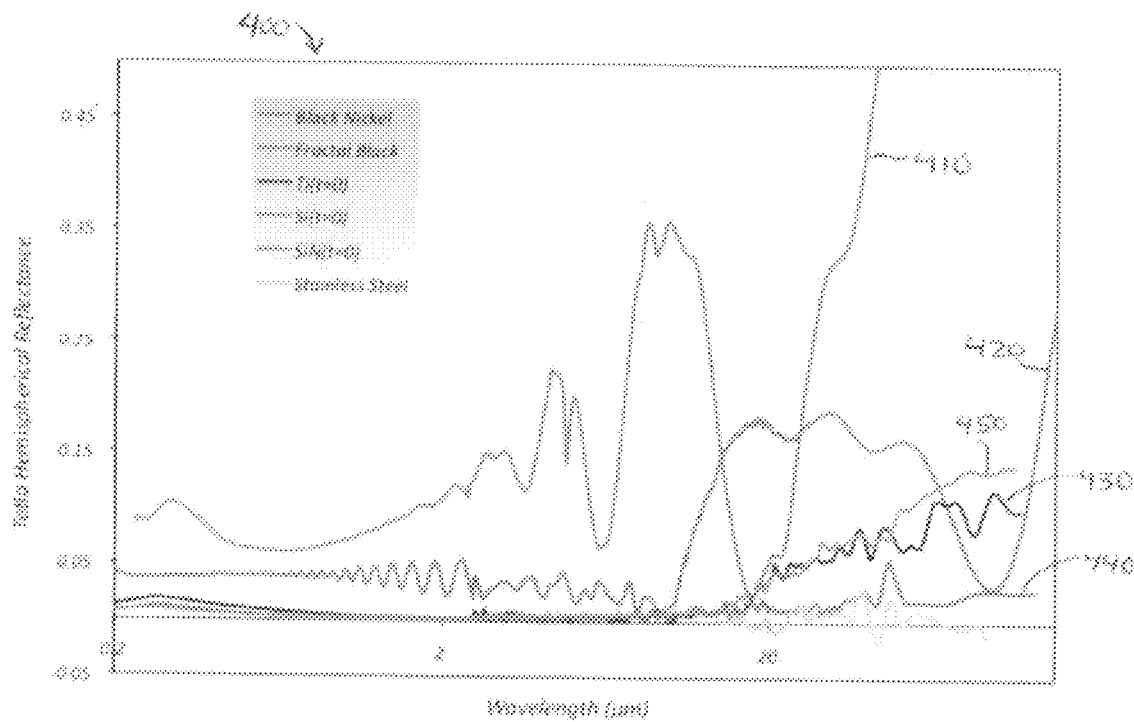
FIG. 4 is a chart illustration of the applicability of the present invention over a wide spectrum, particularly stray light control of infrared to far infrared.

With reference now to FIG. 4 of the Drawings, there is illustrated another chart, generally designated by the reference numeral 400, demonstrating the improvements of the present invention over the prior art. This chart further demonstrates the improved performance of carbon nanotubes versus other known "black" materials. Indeed, the extremely low hemispherical reflectance properties of carbon nanotubes, as employed in the instant invention, have been shown cut to a wavelength of 120 microns and beyond.

As shown in FIG. 4, prior art black nickel 410 and fractal black 420 have very high reflectance properties vis-à-vis the very low reflectance shown with titanium 430, silicon 440, silicon nitrate 450 and stainless steel 460 embodiments of the present invention, details of which are set forth hereinabove and hereinbelow. Further, the greatly improved properties of the present invention thus enable uses in other applications, such as stray light control of infrared to far infrared wavelengths, and near-ideal radiators, calibrators and absorbers for infrared detectors.

In another aspect of the present invention, in a preferred embodiment, a Chemical Vapor Deposition (CVD) technique is employed to grow vertically-aligned nanotubes. As discussed further hereinbelow, this technique incorporates three stages: a) preparation of catalyst, b) nucleation phase (organization of particles and beginning of growth) and c) growth (steady state extrusion from particle at set time). It has been found that, by controlling the $H_2$ exposure time, one is able to tune the diameters and areal densities of the nanotubes. The experimentation described in more detail hereinbelow focuses on the nucleation phase and growth to achieve optimization.

As noted, the present invention is directed to techniques that suppress the stray light encountered in various optical instrumentation. A purpose of the present invention is to optimize the growth of catalyst-assisted chemical vapor deposition-grown carbon nanotubes for use as photon absorbers in mid- to far-infrared applications. As noted, improvement of the height and density of the carbon nanotubes increases the films' absorptivity, bringing this material closer to an ideal absorber. Accordingly, NASA is currently exploring the use of this technology towards improving the stray light suppression of space flight instruments for future earth and space science missions. Detrimental to these scientific instruments is the stray light that scatters on interior telescope and instrument surfaces, thereby reducing the performance of observational instruments.

In order to control this undesired effect, low-reflectance surface treatments implemented into structural instrument designs. As noted, Z306 black paint is traditionally applied and used to absorb stray photons, but advanced absorbers that employ films of multi-walled carbon nanotubes (MWCNTs)

of the present invention have been shown to provide an order of magnitude improvement over current surface treatments, e.g., in the UV-visible-near infrared wavelengths of 200 nanometers to 120 microns.

In the instant invention, a method of optimization for nanotube films is described that extends the order of magnitude improvement to spectral wavelengths greater than 2 micrometers using the aforementioned catalyst-assisted chemical vapor deposition (CVD) technique. To this end, the instant invention varies the thickness of an Iron catalyst layer and deposition conditions; and varies hydrogen pretreatment of substrates to optimize the MWCNT length and film density for efficient absorption of longer wavelength photons. Scanning electron microscopy is preferably used to characterize film density and MWCNT height, and hemispherical reflectance measurements are used to quantify performance of the absorptive films.

In addition, the emissivity, that is the ability of this formulation of carbon nanotubes on these substrates to radiate absorbed energy as a black body, approaches that of an ideal black body radiator. Applicants found that the emittance of carbon nanotube samples grown on titanium, stainless steel and silicon, pursuant to the present invention, tested at various temperatures are far superior to Z306 and other materials, such as black nickel and fractal black, as discussed hereinabove in connection with FIG. 4. The improved properties of the instant formulations are further illustrated by reference to FIG. 5 of the DRAWINGS, which shows a plot of emittance over temperature, generally designated by the reference numeral 500.

Figure 5:
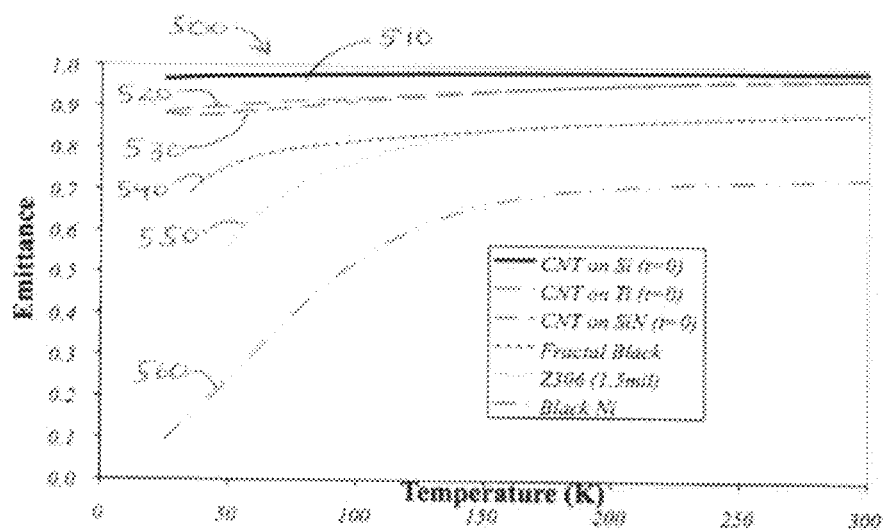
FIG. 5 illustrates the emittance properties of compositions pursuant to the teachings of the present invention.

As shown, the emittance properties of the carbon nanotubes on silicon, generally designated by the reference numeral 510, titanium, generally designated by the reference numeral 520, and silicon nitride, generally designated by the reference numeral 530, are considerably superior to those of fractal black, generally designated by the reference numeral 540, Z306, generally designated by the reference numeral 550, and black nickel, generally designated by the reference numeral 560. This makes the formulations 510, 520 and 530 of nanotubes near ideal for use as calibrators that serve as highly accurate references for scientific observations. As also shown in FIG. 5, the preferred carbon nanotube formulations also perform as a near ideal radiator from ambient to cryogenic temperatures. In fact, Applicant found that the emittance measured is the highest known for any materials at room and cryogenic temperatures.

Experimental Technique

A Physical Vapor Deposition (PVD) deposition was used for deposition of alumina ($Al_2O_3$) and Iron (Fe-catalyst) in a study of the present invention. A 60 nm thick layer of $Al_2O_3$ followed by a layer of Fe with a varying thickness range of 2, 4, 6, 8, 10 nm were deposited. Silicon (Si) and Titanium (Ti) were used as substrates (130 $mm^2$) in the experimentation. Prior to PVD deposition the substrates were sonicated in acetone followed by sonication in isopropyl alcohol (IPA), then blow dried with an air stream. To perform PVD, the samples were placed in a three zone atmospheric-pressure furnace, operating at a temperature of 750° C., with a fused silica tube which has an internal diameter of 1 inch. Flows of Argon gas (inert), $C_2H_4$ gas (feedstock) and $H_2$ gas (vapor etchant) were introduced into the furnace. Additionally, $H_2O$ vapor was added during growth. The experiments varied the flow time of the $H_2$ gas at 5 minutes (t–5) prior to $C_2H_4$ gas, at the same time (t=0) as the $C_2H_4$ gas, and 5 minutes after (t+5) the $C_2H_4$ gas was introduced. The multi-walled nanotubes were then grown for 15 minutes.

Results and Discussion

Figure 6:
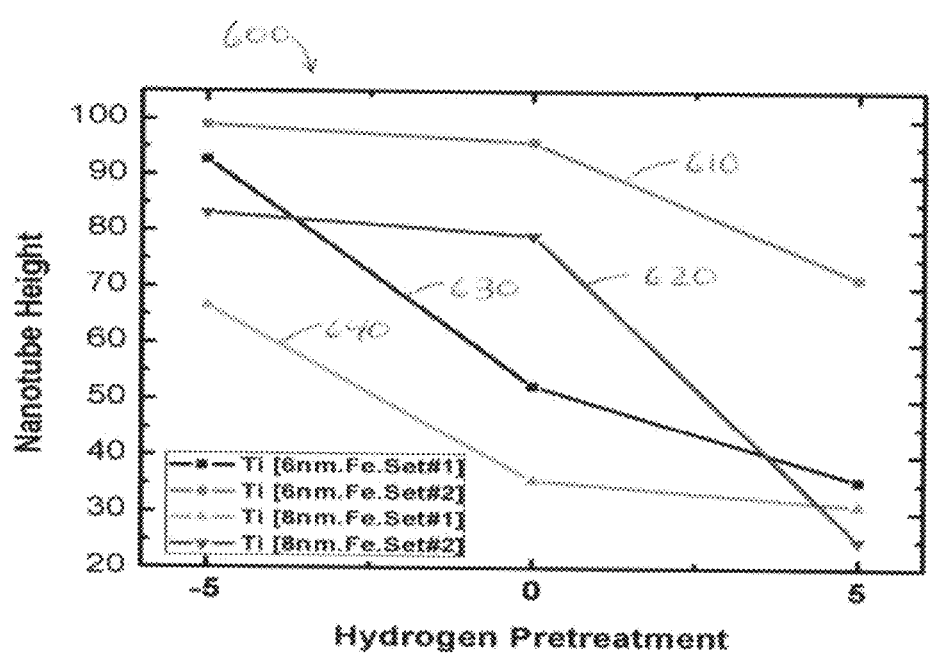
FIG. 6 is still another chart illustration, particularly of the heights of carbon nanotubes generated by the present invention as a function of the hydrogen pretreatment time for various samples.

With reference now to FIG. 6 of the DRAWINGS, there is shown a chart, generally designated by the reference numeral 600, illustrating the nanotube heights verses the aforementioned hydrogen pretreatment for nanotubes grown on the Ti substrate. For the t–5 $H_2$ pretreatment of a first set of samples, designated by the reference numerals 610 and 620, the nanotubes have a length of ~100 nm for samples with 6 nm of Fe (610) and ~83 nm for samples of 8 nm Fe (620) deposited.

For a second set of samples at the t–5 $H_2$ pretreatment, designated by the reference numerals 630 and 640, these heights decrease to ~93 nm and 67 nm respectively, as shown in FIG. 6. It should be understood that both sets of samples were grown during separate PCD or CVD growth runs. As the pre-treatment time increased, the heights of the nanotubes began to decrease. As shown in FIG. 6, the shortest nanotubes were recorded with the t+5 $H_2$ pretreatments. The decrease in length may be attributed to several factors: (a) $H_2$ treatment may be shortening the nanotubes, (b) amorphous carbon and (c) growth termination due the catalyst being embedded deeper into the $Al_2O_3$ layer. It should also be noted that the less catalyst that is deposited onto the substrates, the longer the nanotubes should be. Applicant believes that thinner catalyst layers result in smaller nanoclusters with wider spacing for nanotube growth nucleation. The expected limit for this improvement is at approximately 1 nm thickness for the catalyst layer.

Scanning Electron Micrograph images of MWNTs grown on the Ti and Si substrates show differences between the substrates. For the Ti samples, the height varies due to the roughness of the substrate. For the Si substrates the growth has more uniformity. For the present invention, longer nanotubes were more of interest, which would translate into an increase in the absorptivity. For this reason, the t–5 $H_2$ pretreatment was determined to be the growth process of choice, and that rougher substrates may be more beneficial due to their effective lower density at the nanotube air/vacuum interface.

Figure 7A:
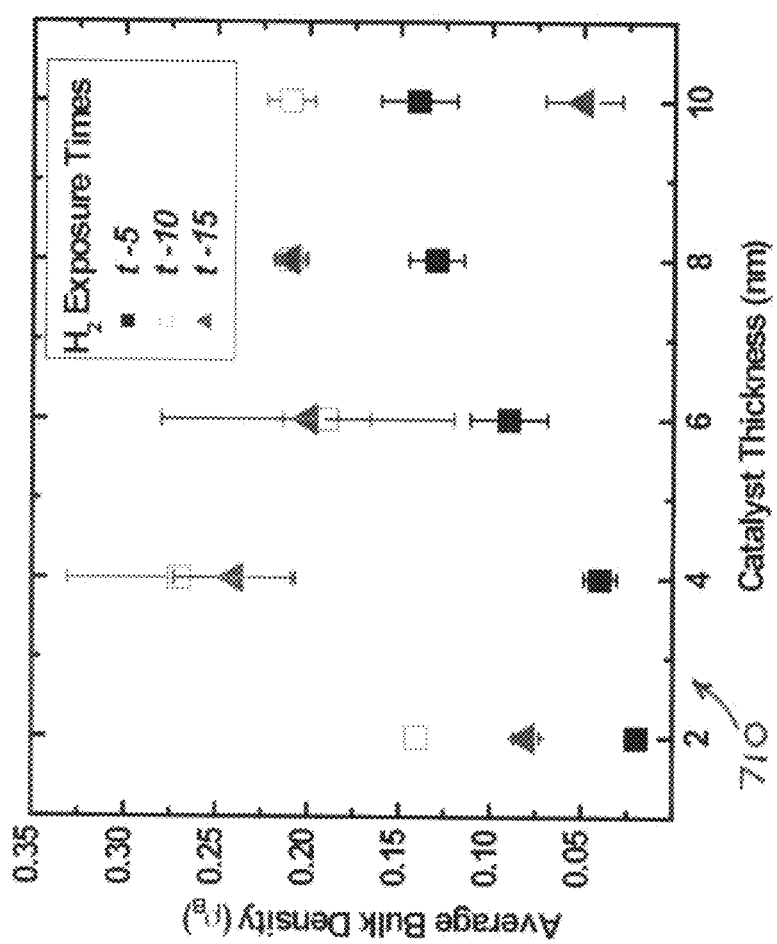
FIGS. 7A-7D illustrate, respectively, average bulk density versus catalyst thickness data plots for various catalyst samples, hemispherical reflectance versus density, density and absorption, and density versus absorption depth, pursuant to the teachings of the present invention.
Figure 7B:
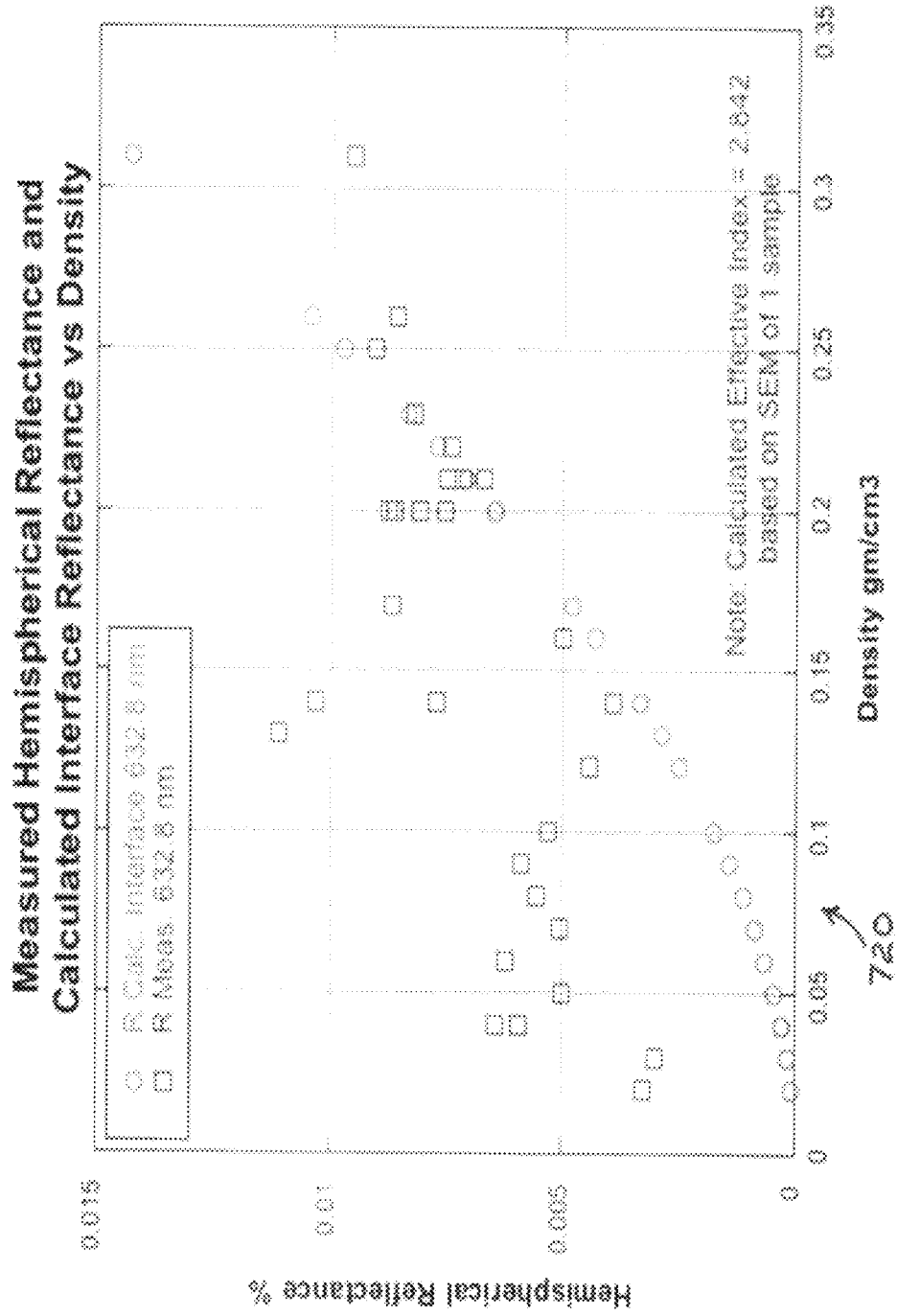
Figure 7C:
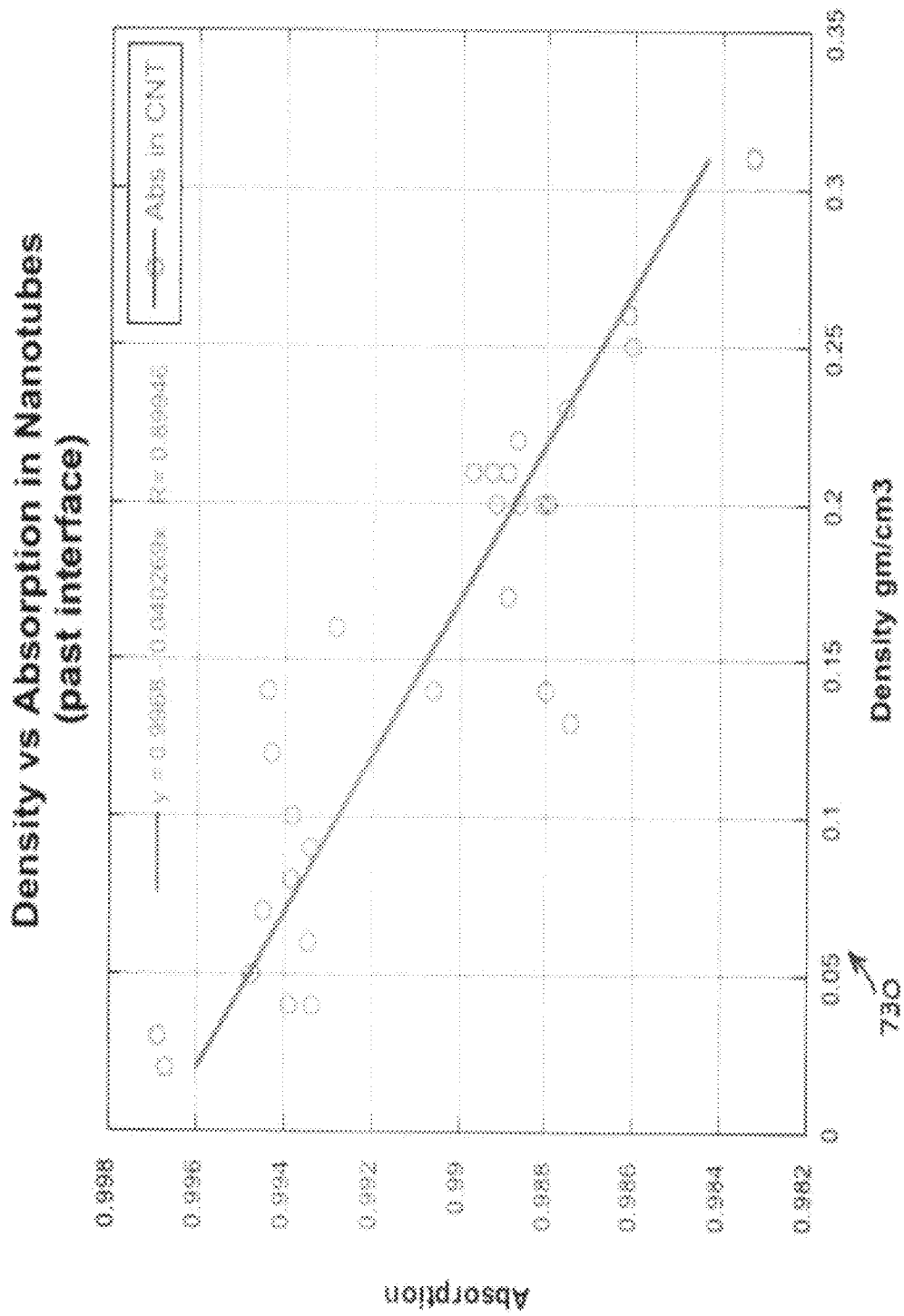

With reference now to FIGS. 7A-7D of the DRAWINGS, there are illustrated various relationships that better describe the nature of the present invention to those of skill in the art. With reference to FIGS. 7A-7C, these charts show the relationship between catalyst thickness and density, designated by reference numeral 710, density and reflectance, designated by reference numeral 720, density and absorbance, designated by reference numeral 730, respectively. The fourth chart, FIG. 7D, designated by reference numeral 740, shows that the light is all absorbed within the first 10 microns of the nanotube layer in the visible. So, heights as low as 50 microns are fine out the far infrared (FIR).

Figure 7D:
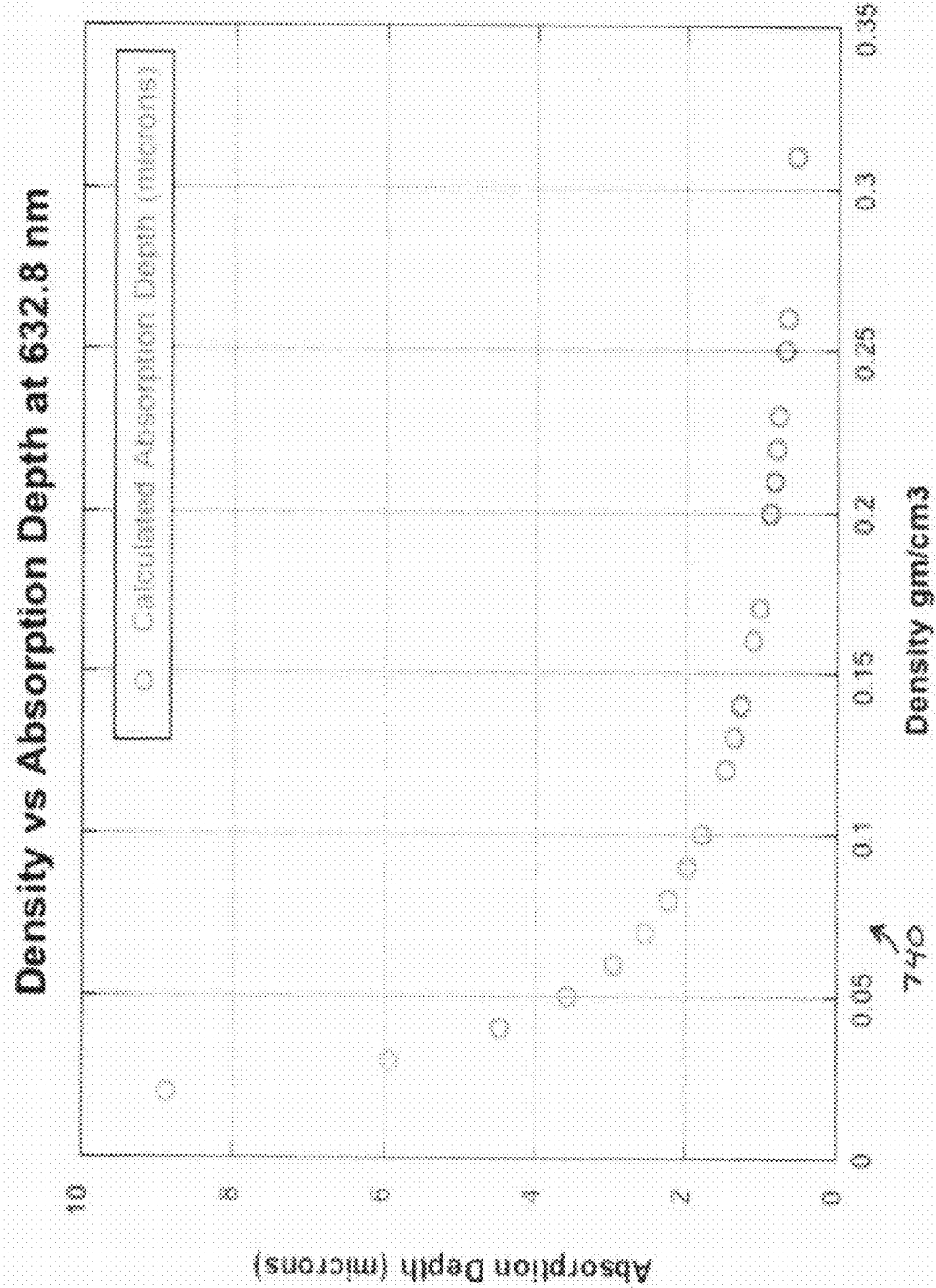

As shown in FIG. 7A, i.e., the relationship between low density and thin catalyst, the 2 nm measure is the best, at t–5 hydrogen pre-treat. Here the density optimization was achieved by tuning the catalyst thickness and the duration of hydrogen pre-treat to reduce the the degree of oxidation of the catalyst layer. As shown in FIG. 7B, this measures hemispherical reflectance and calculated interface reflectance against density, and shows that lower density results in lower interface reflectance. FIG. 7C illustrates density against absorption in the carbon nanotubes (past interface), and shows that lower density results in better absorbance with the carbon nanotubes. Finally, FIG. 7D illustrates density against absorption depth at 632.8 nm wavelength. As recently uncovered by Applicant, the t–5 growths were about 60 microns tall, and calculations show that the in the visible light range all of the light is absorbed in the first 10 microns of the carbon nanotube thickness. Further, measurements of these samples at 120 microns show that less than 0.2% is reflected, where double pass means that the light actually sees about 120 microns of nanotube thickness. As clearly shown by these samples and charts, the materials of the present invention are far blacker than any of the prior art black compositions, making the present invention ideally applicable in a wide range of applications.

By way of conclusion in this study, it was demonstrated that the t−5 $H_2$ pre-treatment is the most effective treatment to obtain longer nanotubes for use in the applications of the present invention. The correlation of $H_2$ pretreatment and nanotube height has been demonstrated, as well as, that substrate roughness affects the growth of the MWNTs. Furthermore, the HR data for the various catalyst thickness samples are promising for further investigation into the far infrared. This data obtained further aids in advancing this technology in NASA's goals of increased instrument performance.

Figure 8:
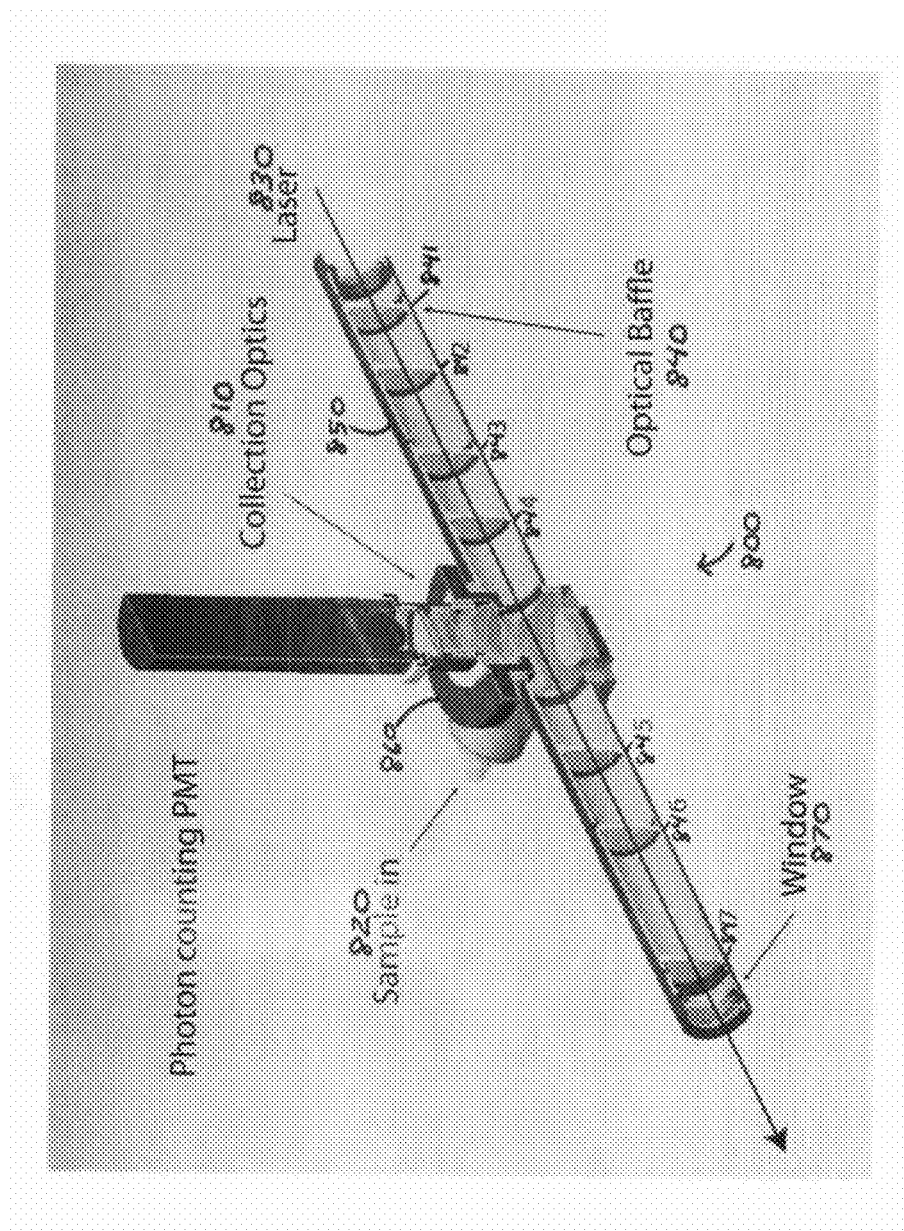
FIG. 8 illustrates an exemplary embodiment of a usage of the improvements of the present invention for suppressing stray light and for energy radiation.

With reference now to FIG. 8 of the DRAWINGS, there is shown a device, generally designated by the reference numeral 800, employing aspects of the instant invention. As shown, device 800 in the embodiment is laser induced fluorescence device to measure photon counts. For example, a center sampling portion of the device 800, generally designated by the reference numeral 810, encloses the collection optics, photo detectors and other devices useful for such counting, e.g., photomultipliers. A sample is introduced into the central sampling area via a passage 820, and a laser (not shown) emits a beam 830 through a measurement tube 850 containing a number of baffles, designated by the reference numerals 841-847 and generally designated by the reference numeral 840. Each baffle 840 has a hole therethrough to allow the aforesaid laser beam to pass through the tube 840, passing through the central sampling area 810. For example, the air within the sample area 810 becomes excited by the laser energy and formaldehyde therein fluoresces and that energy is measured.

With further reference to FIG. 8, the deleterious effects of stray light onto such a measurement are manifest, particularly where small photon counts are expected. Through coating or covering the baffles 840 along the aforementioned hole or entirely, and either all the baffles 840 or at least those immediately adjacent the central area, i.e., baffles 844 and 845, any stray light entering the measurement tube 850 are prevented from entering the central sampling area 810. As shown, windows or other transparent coverings may be employed at the ends of the measurement tube 850, as generally designated by the reference numeral 870. Indeed, compared with the baffles covered with Z306 paint, the baffles 840 of the present invention exhibited over a 6 dB improvement of signal to noise, demonstrating the marked improvement of the instant invention over the prior art.

With further reference to FIG. 8 of the DRAWINGS, there is illustrated another aspect of the present invention, i.e., the improved emittance or radiating properties, as also discussed hereinabove in connection with FIG. 5. As discussed, the multi-walled carbon nanotubes of the present invention have enhanced properties of emittance or energy radiation. Thus, sensitive electronics, which perhaps generate their own heat, are endangered through their own operations without the additional heat sinks or radiators to conduct that heat or energy away. The present invention, particularly the multi-walled carbon nanotubes, has been found to exhibit considerable ability to so conduct heat. Thus, sensitive electronics or anything susceptible to heat or energy damage are better protected by the employment of the principles of the present invention.

Thus, any electronic measurement equipment within the central sampling area 810 may generate heat, which, in turn, could interfere with the photo counting. Through the inclusion of a surface with the aforementioned multi-walled carbon nanotubes thereon, generally designated by the reference numeral 860, the aforedescribed electronics can he protected by the carbon nanotubes drawing the heat away. For example, one end of the vertically-aligned multi-walled carbon nanotubes can face the "hot" part of the chamber 810 and the other end of the carbon nanotubes, disposed away from the chamber 810, can dissipate or radiate the absorbed energy away from the sensitive area.

In like fashion, the heat sink capacities of the present invention can be employed in many other situations where heat must he displaced or moved from one point to another. Although the instance of an electronics embodiment is disclosed, it should be understood that the principles of the present invention may be made applicable in many other situations with similar needs and not just those of electronics. For example, in space exploration, the need to radiate unwanted energy is manifest, e.g., when near the Sun or other energy source, the side facing the emitting object may have measurement apparatus. The energy absorption and radiation properties of the present invention permit probes and other instrumentation to remove excess heat, thereby protecting the delicate electronics or chemicals therein. Further usages of the instant invention are thus envisioned and within the scope of the present application and the claims.

It should be understood that the principles of the present invention may be made applicable in a wide range of situations, not necessarily the extremes of space exploration, the subject of many of the studies herein. Indeed, the present invention may be employed not only in earth's (or other extraterrestrial bodies') atmospheres, but also in countless ground-based applications where light sensitivities govern, such as cameras and the like. The control of stray light is of critical importance in many optical instruments, and the principles of the present invention for reducing the deleterious effects of that stray light are thus useful in a wide context.

While the foregoing written description of the invention enables one of ordinary skill to make and use what is considered presently to be the best mode thereof, it should be understood that various changes, substitutions and alterations can be made herein without departing from the spirit and scope of the invention as defined by the appended claims. Therefore, the invention is not to be limited by the above described embodiment, method, and examples, but by all embodiments and methods within the scope and spirit of the invention as claimed.

We claim:

1. A multi-walled carbon nanotube device for measurement comprising:
   a housing for a sensor, said housing with improved broadband absorption properties having at least one surface adjacent a receptor for said sensor,
   wherein said at least one surface is coated with adhesion improved coated multi-walled carbon nanotubes,
   whereby stray light scattering into said receptor is minimized;
   adhesion and catalyst refining layers to optimize a multi-walled carbon nanotube growth process;
   multi walled carbon nanotubes adhered on titanium and stainless steel, while maintaining broadband absorption;
   alumina as an excellent adhesion layer for nanotubes grown on titanium, stainless steel and silicon wherein the alumina adhesion layer is greater than 60 nanometers thick to optimize performance by including a 10 minute annealing means immediately after growth at 750 C to 950 C, allowing better anchoring of nanotubes into an alumina layer as determined by measuring hemispherical reflectance on a silicon and titanium sample before and after testing; and an electron beam evaporation layer applied immediately prior to the deposition of an iron catalyst layer of a thickness of iron of 1 to 2 nanometers while maintaining vacuum to provide a robust durable coating.

2. The device according to claim 1, wherein said at least one surface is a component selected from the group consisting of absorbers, apertures, arrays, baffles, calibrators, detectors, imaging, laser cavities, radiators, mirrors, reflectors, stops, telescopes, tubes, windows, and combinations thereof.

3. The device according to claim 1, wherein said device is employed in space featuring a zero gravity and vacuum environment.

4. The device according to claim 1, wherein said carbon nanotubes absorb electromagnetic wavelengths from about 0.2 microns to about 120 microns.

5. The device according to claim 4, wherein said carbon nanotubes absorb electromagnetic wavelengths from about 0.2 microns to about 2 microns.

6. The device according to claim 4, wherein said carbon nanotubes absorb electromagnetic wavelengths from about 2 microns to about 120 microns.

7. The device according to claim 1, wherein a substrate of said at least one surface is selected from the group consisting of titanium, silicon, silicon nitrate, copper, stainless steel, chromium, molybdenum and combinations thereof.

8. The device according to claim 1, wherein a thin-film layer of aluminum oxide or sapphire and Iron is deposited on said substrate before the multi-walled carbon nanotubes.

9. The device according to claim 1, wherein said multi-walled carbon nanotubes are substantially vertically aligned to said substrate.

10. A method for coating multi-walled carbon nanotubes on a surface comprising:

depositing an alumina and Iion layer onto a substrate for a component;

growing adhesion improved multi-walled carbon nanotubes onto said alumina layer, wherein said substrate comprises a component adjacent a measurement means, whereby stray light scattering into said measurement means is minimized;

refining of adhesion and catalyst lavers to optimize a multi walled carbon nanotube growth process;

adhering multi-walled carbon nanotubes on titanium and stainless steel, while maintaining broadband absorption;

providing alumina as an excellent adhesion layer for nanotubes grown on titanium, stainless steel and silicon wherein the alumina adhesion layer is greater than 60 nanometers thick to optimize performance by including a 10 minute annealing step immediately after the growth at 750 C to 950 C, allowing better anchoring of nanotubes into the alumina layer as determined by measuring hemispherical reflectance on a silicon and titanium sample before and after testing;

applying electron beam evaporation immediately prior to the deposition of an iron catalyst layer of a thickness of iron of 1 to 2 nanometers while maintaining vacuum to provide a robust durable coating.

11. The method according to claim 10, wherein said substrate is selected from the group consisting of titanium, silicon, silicon nitrate, copper, stainless steel, chromium, molybdenum and combinations thereof.

12. The method according to claim 10, wherein said alumina layer is deposited by electron beam evaporation.

13. The method according to claim 10, wherein said step of depositing deposits a thin film alumina and Iron layer.

14. The method according to claim 13, wherein said thin film alumina layer is about 60 nm thick and said Iron layer is about 2-10 nm thick.

15. The method according to claim 10, wherein said multi-walled carbon nanotubes are deposited onto said alumina layer in a furnace by chemical vapor deposition.

16. The method according to claim 15, wherein said step of growing comprises:

introducing feedstock gases into said furnace, said feedstock gases comprising ethylene and hydrogen gas.

17. The method according to claim 16, wherein said furnace operates at about 750 degrees Centigrade.

18. The method according to claim 16, wherein said hydrogen gas is added at about five minutes prior to the introduction of the ethylene.

19. The method according to claim 10, wherein said multi-walled carbon nanotubes are substantially vertically aligned to said substrate.

* * * * *